US006652798B1

(12) United States Patent
Edvardsson (10) Patent No.: US 6,652,798 B1
(45) Date of Patent: Nov. 25, 2003

(54) METHOD AND AN APPARATUS FOR FORMING AIR-LAID FIBROUS ABSORBENT CORES (75) Inventor: Gunnar Edvardsson, Bohus-Bjorko (SE)

(73) Assignee: SCA Hygiene Products AB, Gothenburg (SE)

( * ) Notice: Subject to any disclaimer, the term of this patent is extended or adjusted under 35 U.S.C. 154(b) by 416 days.

(21) Appl. No.: 09/722,015

(22) Filed: Nov. 27, 2000

Related U.S. Application Data (63) Continuation of application No. PCT/EP99/03628, filed on May 26, 1999.

(30) Foreign Application Priority Data

May 28, 1998 (DE) .......................................... 198 23 954

(51) Int. Cl.[7] ................................................ A61F 13/15
(52) U.S. Cl. ........................ 264/510; 264/517; 264/112; 264/113; 425/81.1
(58) Field of Search ................................ 264/113, 510, 264/517, 112; 425/81.1; 19/145

(56) References Cited

U.S. PATENT DOCUMENTS

| 3,943,605 A | * | 3/1976 | Nystrand ...................... 19/145 |
| 4,598,441 A | | 7/1986 | Stemmler ..................... 19/145 |
| 4,908,175 A | * | 3/1990 | Angstadt ..................... 264/113 |
| 4,927,346 A | | 5/1990 | Kaiser et al. ............... 425/81.1 |
| 5,064,484 A | | 11/1991 | Craig et al. ................. 156/62.6 |
| 5,762,844 A | * | 6/1998 | Van Himbergen et al. .. 264/112 |

FOREIGN PATENT DOCUMENTS

| DE | 3413925 A1 | 10/1985 |
| DE | 4335919 A1 | 4/1995 |
| EP | 0292624 A1 | 11/1988 |
| EP | 0627211 A1 | 12/1994 |
| FR | 2690843 A1 | 11/1993 |
| GB | 2124264 A | 2/1984 |
| GB | 2294703 A | 5/1996 |
| GB | 2315220 A | 1/1998 |
| WO | WO 9510994 | 4/1995 |

* cited by examiner

Primary Examiner—Mary Lynn Theisen
(74) Attorney, Agent, or Firm—Young & Thompson (57) ABSTRACT A method and an apparatus for forming air-laid fibrous absorbent cores comprises a first supply of air-entrained fibrous material and a first air-laying element connected with the first supply of air-entrained fibrous material and having a movable first perforated forming element for forming a first air-laid component of the absorbent core. Further, a supply of air-entrained fibrous material and discrete particles of absorbent material and a second air-laying element connected with the supply of air-entrained fibrous material and discrete particles is provided. The second air-laying element has a movable second perforated forming element for forming a second air-laid component of the absorbent core comprising a mixture of dispersed fibrous material and discrete particles and the second air-laying element is positioned with respect to the first air-laying element such as to transfer a formed second component from the second forming element onto a formed first component on the first forming element.

37 Claims, 3 Drawing Sheets

FIG. 2

FIG. 3

METHOD AND AN APPARATUS FOR FORMING AIR-LAID FIBROUS ABSORBENT CORES

This is a continuation of International Application PCT/EP99/03628 filed May 26, 1999, which designated the United States.

FIELD OF THE INVENTION

The present invention relates to a method and an apparatus for the manufacture of absorbent cores or pads for absorbent articles such as disposable diapers, sanitary napkins, incontinence pads and the like. More particularly, the present invention relates to an apparatus for forming multi-layered absorbent cores by the air-laying technique.

Multi-layered absorbent cores in accordance with the present invention comprise at least two layers of air-laid fibrous material webs, one of the layers being superimposed on the other and comprising fibers mixed with discrete particles. The fibers of the respective layers can be the same or different and consist of hydrophilic or hydrophobic fiber material or a mixture of both. Additionally, the fibers can comprise a cellulosic or chemical pulp. The discrete particles are provided to enhance the absorbing property and the ability to retain body fluids and wastes, also under pressure, and generally comprise an absorbent gelling material in the form of hydrogel particles. PreferablY, the absorbent gelling material comprises so-called superabsorbent. However, the type of fiber and discrete particles of absorbent gelling material does not form an essential part of the present invention and any combination thereof suitable for the intended purpose of the absorbent core can be selected.

For the purposes of the present invention, a standard absorbent article has at least a dual-layer or triple-layer absorbent core wherein an outer (first) or both outer (first and third) layers are formed by a shaped core component essentially consisting of an air-laid fibrous material web. An inner or middle core (second) substantially uniform mixture of fibrous material and discreted particles of absorbent material. The outer layer or layers generally define the shape of the absorbent core and follow the shape of the absorbent article in which the core is incorporated. The insert or middle core layer can either have the same shape as the outer layer or layers or it can have a smaller shape and be placed at a location where the body fluid or liquid absorption and retaining properties thereof are most desired and beneficial in the absorbent article incorporating it.

BACKGROUND OF THE INVENTION

An apparatus for the manufacture of multi-layered absorbent pads is known from U.S. Pat. No. 4,598,441. In order to produce a dual-layer absorbent pad, two air-laying apparatus respectively in the form of rotatable drums with perforated forming moulds on their peripheries are provided to form the two fibrous web layers. A first transfer roll is provided between the two air laying drums and picks up a formed first fiber web from the first air-laying apparatus and places this on a second fiber web already formed on the second air-laying drum. This dual-layer absorbent pad is then removed by a further transfer roll from the second air-laying drum and placed on a conveyor for further processing. An optional feature of this known apparatus is the placement of an insert between the two main fiber layers, said insert possibly being a superabsorbent medium. The superabsorbent medium is applied as a discrete layer in powdered or granulated form on the first fiber web while the latter is transferred on the first transfer roll from the first to the second air-laying drum. Suction boxes are provided inside the respective cylinders forming the air-laying drums and the transfer rolls to maintain the fiber layers thereon while they are being transported through the apparatus. However, the air-laying of a fibrous web substantially uniformly mixed with discrete particles of superabsorbent is not disclosed. In any case, this known apparatus is not suitable for producing an absorbent core comprising such a fibrous web uniformly mixed with discrete particles because such particles would fall out along the long path of conveyance through the apparatus. Additionally, the known apparatus is relatively bulky.

Another example of a method and an apparatus for forming-air-laid fibrous absorbent cores is known from FR-A-2 690 843. A first supply of air-entrained fibrous material is deposited on a first movable forming element, and a second supply of air-entrained fibrous material is deposited on a second movable forming element. Subsequently, the first formed component is positioned on an assembly cylinder, and the second formed component is positioned onto the first formed component on the assembly cylinder. In addition, the device comprises a transfer cylinder to transfer the absorbent cores to a conveyor belt. However, the. manner in which superabsorbent material could be included and whether such material was dispersed with the fibrous material or not is not disclosed. Moreover, the apparatus according to FR-A-2 690 843 is relatively bulky as well because of the additional assembly and transfer cylinders.

A method and an apparatus for forming absorbent cores or pads is also known from GB-A-2 124 264. The absorbent core comprises two layers of air-laid fibrous webs which may be of the same or different types. Separate streams of air-entrained fibers are air-laid on an endless perforated belt at locations spaced from each other along the moving belt to form a layered pad. Air from the air-entrained fiber streams is removed via a vacuum chamber disposed beneath the perforated belt.

However, various problems arise in air-laying absorbent cores with a multiplicity of layers including one or more layers containing a mixture of fibers and discrete particles. As the air must be removed from beneath the perforated forming element of the air-laying apparatus, some of the discrete particles mixed with the fibers can be drawn through the perforated forming element so that these particles, which may consist of expensive absorbent gelling materials, are lost. This has the additional disadvantage that the absorbent core is reduced in absorbent capacity. A further problem that can arise is the blocking of air flow through the perforated forming element by larger absorbent particles lodged in the perforations so that the finished absorbent pad does not have the desired structure.

These problems are partially solved by a method and an apparatus disclosed in EP-A-0 292 624 for forming air-laid absorbent cores having a multiplicity of layers. For an absorbent core comprising two main layers, air-entrained fibrous material is split into streams and fed to two separate air-laying apparatus arranged along a conveyor system. In the first drum-type air-laying apparatus for producing the layer comprising a fibrous web mixed with discrete particles of an absorbent gelling material, a so-called dusting layer is first formed by blowing a first air-entrained fiber stream onto the perforated forming element of the air-laying apparatus. A main stream of air-entrained fibrous material mixed with discrete particles is then blown onto the dusting layer to form the main fibrous layer mixed with the discrete particles.

The dusting layer acts as a filter screen to prevent passage of small discrete particles through the forming element and prevent large particles from plugging the openings therein.

However, the method and apparatus known from EP-A-0 292 624 have various disadvantages. The final absorbent core is produced from the respective fibrous webs formed in the two air-laying apparatus located at a distance from each other in that the two formed webs are placed on separate endless conveyor belt systems and conveyed from there to a location at which they are only then united to produce the finished absorbent core. Therefore, the speed of the arrangement is limited as too high a speed of the respective conveyers may result in the fibrous webs located thereon being damaged or lifted off the conveyor due to air resistance. Further, the apparatus as a whole takes up a lot of space and requires a complicated and expensive conveying system. A particular disadvantage also lies in that the fibrous web comprising the discrete particles must travel long distances along which particles can fall out of the web so that the final absorbent core will have a reduced absorbent capacity. Although this fibrous web mixed with particles can be enwrapped in tissue or the like before being united with the other fibrous web, this process introduces increased complications and costs. Further, the absorbent properties of the final product may be adversely affected by the presence of the tissue and such tissue hinders the possibility of at least loosely connecting the respective fiber webs to each other to increase the strength of the final product. Finally, the known apparatus does not permit easy uniting of the respective layers in terms of accurate targeting or placement of the fiber and particle web on the second fiber web to form the finished absorbent core.

SUMMARY OF THE INVENTION

It is the object of the present invention to provide an efficient method and apparatus for forming improved air-laid fibrous absorbent cores having at least two layers with at least one layer having fibers with discrete particles dispersed therein.

This object is solved in accordance with the present invention by an apparatus comprising the features of claim 1 and a method. comprising the features of claim 24. Particularly advantageous embodiments of the inventive apparatus and method are described in the dependent apparatus and method claims.

According to the present invention, the apparatus and method provide two separate air-laying means having movable perforated forming elements thereon. The air-laid components making up the absorbent core are separately formed by applying a stream of air-entrained fibrous material or, as applicable, a stream of a mixture of air-entrained fibrous material and discrete particles of absorbent material onto the respective forming element of the respective air-laying means. Thus, the (second) component of the absorbent core formed of the mixture of preferably substantially uniformly mixed fibrous material and discrete particles is formed in a separate (second) air-laying means independently of other (first and possibly third) components of the final absorbent core which are produced on the other (first) air-laying means. This allows the production and processing parameters for forming the mixed second component to be set and adjusted as desired independently of the formation of the other absorbent core components. This avoids having to take disadvantageous limitations into account as, for example, if the mixed second component is formed on the same air-laying means as the other components of the absorbent core.

In particular, the design of the second air-laying means for the mixed second component can be different to the design of the air-laying means for the other components. This especially includes the design of the (second) forming element of the second air-laying means, the supply of the fibrous material and discrete particles thereto and the formation conditions. Thus, the mixed second component of the absorbent core formed on the second air-laying means can have any desirable different size, shape or composition as compared to the other component or components of the absorbent core formed on the (first) forming element of the first air-laying means. Additionally, as compared to the first forming element in the first air-laying means, different perforation sizes in the second and different differential air pressures across said second element can be used to produce the mixed second component.

A particularly important advantage of the inventive apparatus and method results from the transfer of the mixed second component from the second air-laying means onto a first component already formed in the first forming element of the first air-laying means while the first component is still located in the first air-laying means. This provides the particular benefit of simplifying the targeting of the mixed component on the other layer (first component). Further, undesirable excessive mixing of discrete particles in the mixed second component into the underlying first component is substantially avoided as compared to a known method in which the mixed second component is formed directly on the first component already. formed in the same air-laying means.

In this disadvantageous method described above, the second component of mixed fibrous material and discrete particles is applied under pressure onto the first component. Further, an underpressure is possibly also created beneath the formed first component to draw the fibrous material and discrete particles onto this layer to form the mixed second component thereon. This causes disadvantageous migration of particles from the mixed second component layer into the underlying first component layer. The first component layer is usually employed as a so-called acquisition layer in the absorbent core of a final absorbent article such as a disposable diaper and is therefore the first layer of the absorbent core which receives body fluid or waste. If discrete particles of, for example, an absorbent gelling material are present in such an acquisition layer, this can partly lead to rewet or slow the acquisition rate of the body fluid. The discrete particles should preferably only be present in the mixed component layer of the absorbent core as these particles, in the form of an absorbent gelling material, have the primary function of retaining liquid, also under pressure to avoid rewet, at a distance from the location of acquisition where quick removal of fluid from the outer surface of the article is desired. Additionally, absorbent gelling material in the acquisition layer can also lead to so-called gel-blocking of body fluid penetrating through the acquisition layer since swollen gelling material hinders the throughflow of the body fluid.

The present invention avoids all of these problems by forming the mixed second component separately from the first before uniting these. Also, the present invention does this in a particularly advantageous manner by also effectively reducing the loss of expensive discrete particles comprising, for example, absorbent gelling material from the finished absorbent core on account of transferring the second component onto the first component while the latter is still on the first forming element of the first airlaying means. Additionally, transfer of the mixed second component onto the first component while this is still on the first air-laying means permits some interconnection of the components, especially if a third component is subsequently formed on top of the first and second components as in a preferred embodiment of the present invention.

The transfer of the mixed second component onto the first component while this is still on the first air-laying means also contributes to reducing the size and cost of the apparatus and removes the need for a complicated means to unite the components.

In preventing the loss of discrete particles out of the absorbent core after the mixed second component is transferred in the inventive manner onto the formed first component and out of the apparatus as a whole, other problems are also prevented. For example, in an absorbent core for a disposable diaper or the like, the production rate is approximately 600 cores per minute, which corresponds to 10 cores per second, If a core has an average discrete particle weight of 10 g, this implies that the process consumes approximately 100 g per second. If even only approximately 5% of the discrete particles is lost out of each absorbent core during manufacture, then a considerable quantity of-expensive absorbent material is lost over time. Further, these large quantities of particles have to be removed from the apparatus to maintain proper operation thereof. The reduction of the loss of discrete particles according to the present invention overcomes these problems.

Further, as already described, the present invention relates to an absorbent core having a second component comprising a mixture of fibrous material and discrete particles, preferably substantially uniformly mixed. Although it is known in the art to provide absorbent cores with a discrete layer of particles, such a core is disadvantageous in terms of the final performance under wetting of the absorbent core. More importantly, however, in manufacture, the discrete particles are more likely to be lost because they are not dispersed within a fiber web. These problems are also avoided with the present invention.

In an advantageous preferred embodiment of the present invention, a third component of the absorbent core comprising air-laid fibrous material is formed on the united first and second components. This contributes to further reducing. the loss of discrete particles from the absorbent core during manufacture. Preferably, the third component is formed while the first and second components are still positioned on the first forming element of the first air-laying means to prevent loss of any particles as soon as possible and to also reduce the size of the apparatus. Additionally, during formation of the third component, the connection between the three components is strengthened by fibers of each component mingling with each other.

Preferably, the supply of air-entrained fibrous material for forming the first and third components is produced by connecting a source of fibrous material to an air fan which entrains the fibrous material and supplies this to the first air-laying means. Various conventional means may be used as the source of fibrous material. For example, the fibrous material can be produced from fiber sheets passed through a rotary disintegrator and further to the air fan.

Advantageously, the supply of air-entrained fibrous material and discrete particles includes a similar conventional source of fibrous material and any convenient source of discrete particles such as a hopper. Preferably, the fibrous material and discrete particles can be mixed most advantageously in an air fan before being supplied to the air-laying means so that a substantially uniform mixture or dispersion of the particles in a fiber web is produced as the second fibrous component on the second forming element. Even better mixing is achieved by introducing the fibrous material and discrete particles into a duct (104, 204) upstream of the air fan as fiber flocks may otherwise be formed in the fan which no longer mix with the particles.

In accordance with a further advantageous embodiment of the invention, at least one or both of the forming elements of the respective air-laying means comprise one or more cavities or moulds which define the shape of the absorbent core component to be produced. The base of each cavity comprises the perforations of the forming elements upon which the respective fibrous web is formed and trough which the air passes to be separated from the entrained material for forming the component. Further, the cavities can be exchangeable so as to be able to provide different shapes of the components. For example, the first (and possibly third) fibrous component formed on the first air-laying means can have cavities in the shape of an hour glass so as to produce the commonly known shape of a disposable diaper. However, in accordance with the invention, as the second component comprising the mixture of fibrous and discrete particles is formed separately from the first and third components in the separate second air-laying means, depending on the desired design of the final product, the cavities forming the second forming element can be the same size or can be smaller than the cavities of the first forming element when the entire surface of the unfolded diaper comprising. the absorbent core does not require total surface coverage by the second component. This is particularly advantageous in that areas of the mixed second component as compared to the area of the unfolded diaper as a whole can be omitted to avoid material wastage and therefore saves expensive absorbent (gelling) material and fibers. In particular, as viewed in the unfolded state, an absorbent article such as a disposable diaper does not require an absorbent core with a mixed second component of fibrous and discrete particles which extends up to the longitudinal extremities of the article. This is because the fluid wicking effect of the article towards the longitudinal extremities is normally relatively poor and the absorbent material and fibers are not or barely wetted in these areas. The same applies to a lesser extent in respect of the extremities of the article as seen in the direction transversely to the longitudinal extension, i.e. the width of the article. The possibility of accurately positioning a smaller mixed second component in accordance with the present invention while simultaneously preventing loss of discrete particles as described above and further below is therefore a particular advantage of the present invention over prior art techniques for producing absorbent cores with a component of uniforrmly mixed fibers and discrete particles.

The inventive forming of the mixed second component of the absorbent core on a separate second air-laying means also produces advantages in the manufacturing process as compared to previous systems in which a narrower mixed second component is formed in the same air-laying means directly on the first component, which covers the entire width of the forming element.

In the previous system referred to above, a forming duct is provided above the forming element of the air-laying means, the duct having a narrower width than the forming element and the first component which is already present therein. By appropriately positioning the forming duct for the air-entrained mixture of fibers and discrete particles to guide the mixture onto the forming element of the first component, the narrower mixed second component is formed at the desired location. However, as the forming duct for the second component is narrower than the perforated forming element therebeneath, a significant amount of air can escape between the end of the narrower duct and the wider forming element. Air for entraining the fiber and discrete particle mixture is expensive to produce, transport and filter. Further, it is not possible in this type of apparatus to prevent this air loss by closing the exposed area between the narrower forming duct and the wider forming element because this would otherwise result in the second component being formed across the entire width of the forming element, which wastes fiber and discrete particles. Therefore, in a preferred embodiment of the present invention significant advantages in the manufacturing process of the absorbent core are achieved by using a forming duct which has substantially the same width as a narrower cavity in the second forming element of the separate (second) air-laying means because the air loss is substantially prevented.

An additional advantage is provided according to the inventive method and apparatus when using a narrow cavity for the second component. When the second component is transferred and placed on the first component, discrete particles falling out of the sides of the second component are immediately caught by the underlying first component. Therefore, the amount of discrete particles lost in the apparatus is further reduced with little loss of particles into the first component because these are mostly retained by the fibers of the second component.

In a similar manner as described above, forming ducts can also be provided to form the first and third components of air-entrained fibrous material on the first air-laying means and these ducts can have substantially the same width as the cavities in the first forming element so as to prevent loss of air.

The formation the respective components of the absorbent core in the method and apparatus of the present invention can be advantageously controlled by appropriate selection of the differential air pressures across the forming elements and the size of the perforations in the forming elements. The perforations in the first forming element upon which the first and third components are formed should be of a suitable size which represents a compromise between the necessity to provide the air with the easiest possible passage through the forming elements, this advantageously reducing the differential pressure that has to be created across the forming elements, and the need to prevent passage of the air-entrained fibrous material or discrete particles through the forming elements. Therefore, in accordance with the invention, the perforations in the first forming element preferably have a largest dimension perpendicular to the air flow of approximately 1 mm and, more preferably, 0.5 mm. Most preferably, the largest dimension is no larger than approximately 0.2 mm.

On the other hand, as the. mixed second component comprising fibrous material and discrete particles is formed on a separate second forming element in the second air-laying means and air does not have to be drawn through more than one fibrous component, the perforation dimensions in the second forming element advantageously can be smaller than those in the first forming element and the largest dimension is preferably approximately 0.5 mm and, more preferably, 0.2 mm Most preferably, however, the largest dimension is approximately 0.05 mm so as to provide an effective barrier against throughpassage of the discrete particles of, for example, absorbent gelling material such as superabsorbent. Superabsorbents used in absorbent articles normally have a mean average diameter of approximately 0.2 to 0.8 mm so that their passage through the second forming element is effectively reduced or even excluded in the preferred inventive embodiment of the second forming element having its largest perforation dimensions as defined above. Naturally, the present invention is not limited to substantially spherical discrete particles. These can also be of any other regular or irregular shape including oblong or fiber-like shapes.

Preferably, the perforations in the first and second forming elements are formed by a screen such as a wire mesh screen. If required for reasons of strength, the screens can be formed of multiple layers having an increasing mesh diameter in the downstream layers as seen in the direction of air flow, or appropriate support bars can be provided beneath the screen. A combination of layers of mesh screens and support bars is also possible. Naturally, however, the support arrangement must be chosen so as to avoid blocking the air flow as much as possible.

The differential pressure across the forming elements is preferably produced in a known manner by creating a vacuum or underpressure at the downstream side of the forming elements. This underpressure generally improves formation of the fibrous web on the forming element and temporarily maintains the formed web in position until it is to be removed, for example by removing the underpressure and/or creating a differential pressure in the opposite direction to that of the original air flow created during formation and/or using gravitational force. Any means such as a vacuum source in the form of a suction box or the like can be used to create the differential pressures across the forming elements.

The pressures across the first forming element for forming the first (and third) components is approximately 7500 to 9000 Pa, preferably 8500 Pa. However, in accordance with the present invention, the differential pressure for forming the mixed second component of fibrous material and discrete particles in the separate second air-laying means can be considerably higher and is preferably approximately 30000 Pa. This increased pressure provides advantages both in terms of the speed at which the second component can be formed and the final structure of the formed second component.

In a particularly advantageous embodiment of the invention, the second air-laying means is positioned with respect to the first air-laying means such that the mixed second component is transferred directly out of the second forming element onto a formed first component on the first forming element so that there is a minimum distance of transfer and therefore a minimum loss of discrete particles out of the mixed second component during the transfer operation.

In an alternative advantageous embodiment of the present invention to that described above, a transfer means is provided between the first and second air-laying means to transfer the second component onto a formed first component in the first air-laying means. The inventive transfer means comprises at least one pick-up means to pick up the second component and transfer it onto the first component. Even though the transfer path is somewhat longer than the arrangement for directly transferring the second component as described above, the transfer means also provides significant advantages. Preferably, there is a plurality of pick-up means which are each rotatable around the periphery of the transfer means at a variable orbital distance from the axis of rotation of the pick-up means. This provides an improved and positive transfer or delivery of the mixed second component onto a formed first component if the latter lies below the upper surface of a recess or cavity in the first forming element. Consequently, the best possible localisation or targeting of the second component with respect to the first (and subsequently laid third) component in the absorbent core is achieved.

Another advantageous embodiment of the present invention comprises first and second air-laying means with rotatable forming drums on which the forming elements are formed around the periphery of the drums. When the forming elements comprise a plurality of cavities, the rotating drums allow the production of the absorbent cores at a high rate in a relatively small space. Further, the supply of the materials to form the various components can be arranged around the peripheries of the drums to save further space as compared to known arrangements of air-laying means and supplies of material along a straight production path. As already stated previously, the cavities of the respective forming elements can be exchangeable. Therefore, the shape and dimensions of the first, second and third components can be changed as desired by simply exchanging the cavities of the respective forming elements.

In a most preferred embodiment of the present invention, the second forming drum is provided above the first forming drum to achieve a maximum space saving in terms of the length of the production line for an absorbent article such as a disposable diaper or the like. Furthermore, this superimposed relationship of the two drums allows for simple transfer of the second component onto the first component either directly or by way of the transfer means as previously described. Naturally, in this embodiment it is possible to transfer using only the influence of gravity. However, for high production rates and positive targeting or delivery of the second component onto the first component, it is preferable to use vacuum means such as suction boxes or the like within the forming drums for creating differential pressures between the first and second forming elements . so as to consistently accurately transfer the second component onto the first component Alternatively, the transfer means described above can be used to achieve such an accurate transfer.

In another advantageous embodiment of the present invention, the finished absorbent core formed in the first and second air-laying means is received from the first air-laying means by a conveying means or any other means and removed for further processing.

Further advantages of the inventive apparatus and method will become apparent from the following detailed description of preferred embodiments of the present invention with reference to the drawings, in which:

DETAILED DESCRIPTION OF THE INVENTION

In the following description of the drawings, the same components of different embodiments of the present invention are designated with the same reference numerals.

A first preferred embodiment of an apparatus according to the present invention is described in the following with reference to FIGS. 1 and 2. Further, this first preferred embodiment is described with reference to a method in which a triple-layer absorbent core is formed. However, as previously revealed, the method and apparatus according to the present invention applies to any absorbent core which has at least two layers and it will be immediately evident to the skilled person how to modify the described apparatus or alter the process carried out therein to produce an absorbent core having more or less than three layers. In particular, for more than the three layers as described, it is simply required to provide further means for conveying fibrous material possibly mixed with particles onto the forming cavities or molds of the respective air-laying means.

Figure 1:
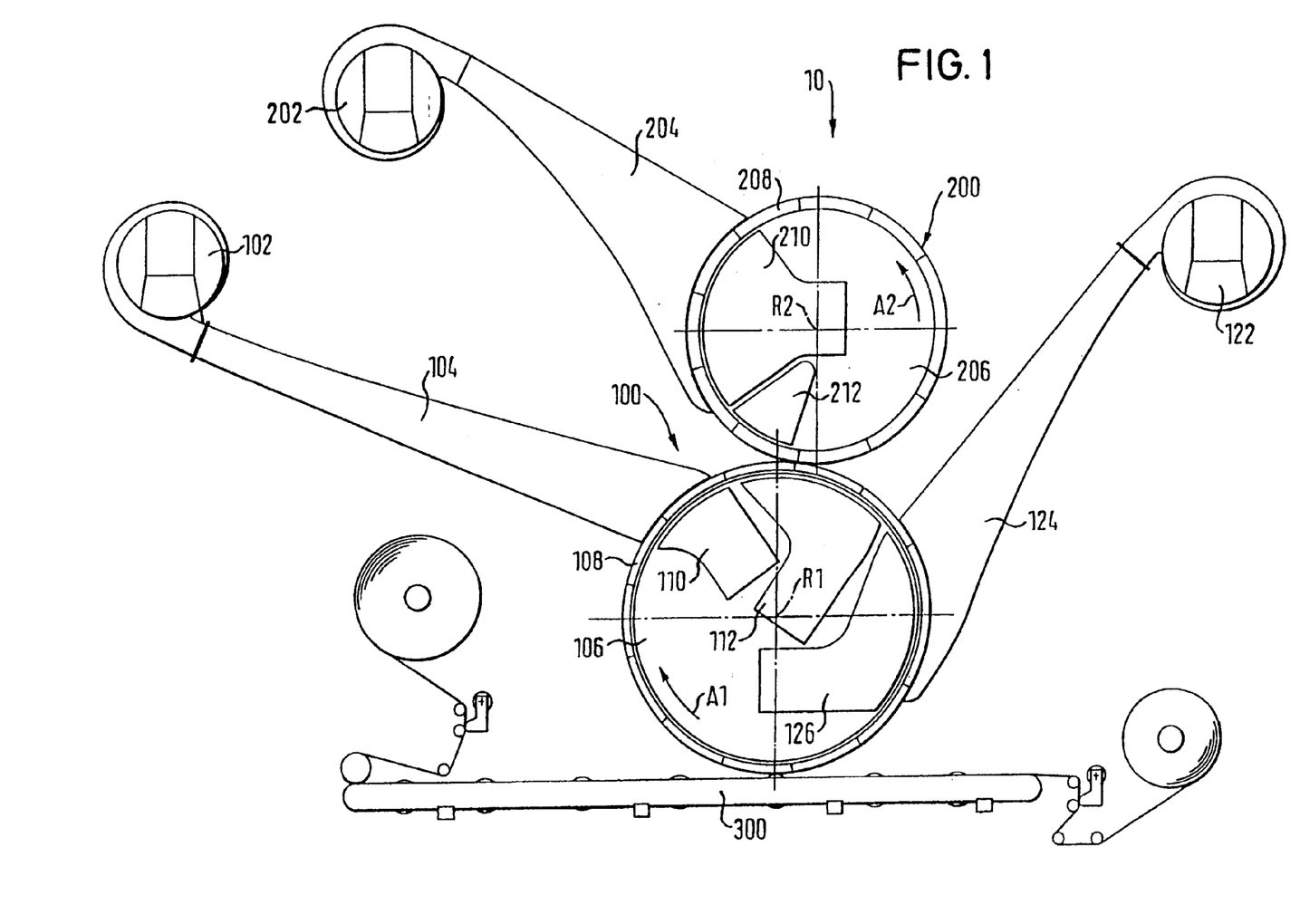
FIG. 1 shows a partially cut-away side view of a preferred embodiment of an apparatus according to the present invention.

With reference to FIG. 1, an apparatus 10 according to the first preferred embodiment of the present invention comprises a first air-laying means 100, a second air-laying means 200 and a conveying means 300 or the like.

The first air-laying means 100 comprises a first air fan 102 which is supplied with fibrous material by any conventional means such as fiber sheets passed through a rotary disintegrator or the like (not shown) to produce fiberized pulp. The fibrous material is transported by air blown by the first fan 102 through a forming duct 104 to a first perforated moveable forming element 106. In this preferred embodiment, the first forming element 106 comprises a substantially cylindrical first drum mounted on a substantially horizontal axis of rotation R1 about which it is driven in the direction of arrow A1 by any suitable drive means (not shown). The shape of the downstream end of the first duct 104 is adapted to the shape of the first forming element or drum 106 and has the dimensions to cover that area of the-first forming element 106 which is required to produce the first fibrous component C1 (see FIG. 2) of an absorbent core on the first drum 106 during rotation thereof, as described in more detail below.

In the first preferred embodiment of the apparatus illustrated in FIG. 1, the first forming element or drum 106 has a plurality of first forming cavities or moulds 108 arranged around its periphery. Optionally, the first cavities 108 can be mounted on the periphery of the first drum 106 to be exchangeable so that any desired shape or size of cavity can be used depending on the desired shape of the first component C1 and the absorbent core itself to be produced.

Inside the periphery of the first drum 106 and the first cavities 108, there is a first means for generating an underpressure 110 in the form of, for example, a vacuum or suction box. The opening of the first suction box 110 facing the periphery of the first drum 106 is shaped and dimensioned to be suitably adapted to the peripheral surface of the first drum 106 and in substantial correspondence with the outlet end of the first duct 104. This permits the optimal conditions to be created for the area and strength of the differential pressure which is created across the first cavities 108 to form the first components C1 of the absorbent core by means of respectively blowing and drawing the fibrous material supplied from the first fan 102 into the first cavities 108.

The features of the first air-laying means 100 described up to now effect the production of the first component C1 of the absorbent core. The separate second air-laying means 200 illustrated in FIGS. 1 and 2 is provided downstream thereof in the direction of rotation A1 of the first drum 106 to produce the second components C2 of the absorbent core which are to be placed on the first components C1.

The second air-laying means 200 comprises a second air fan 202 also connected to a source of fibrous material (not shown) similar to that previously described with reference to the first fan 102. Additionally, however, second fan 202 is connected to a source of discrete particles such as absorbent gelling material to be mixed with the fibrous material in forming the second component C2 of the absorbent core. Advantageously, to achieve a substantially uniform dispersion of fibrous material and discrete particles, both are united upstream of the second fan 202 to be evenly mixed therein. A second duct 204 connects the second fan 202 to a perforated second forming element 206 which is preferably also in the form of a substantially cylindrical drum mounted to be rotated in a direction of rotation A2 about an essentially horizontal axis of rotation R2 which is substantially parallel to and above the rotary axis R1 of the first forming element 106 as seen in the drawing plane of FIG. 1. While the arrangement of the second forming element or drum 206 with respect to the periphery of the first forming element or drum 106 is not an essential part of the present invention, as seen in the drawing plane of FIG. 1, it is advantageously arranged such that the axis of rotation R2 of the second drum 206 is above that (R1) of the first drum 106 and somewhat horizontally displaced to the right in the drawing, i.e. arranged downstream in the direction of rotation A1 of the first drum 106 as seen with respect to a vertical line passing through both axes of rotation and illustrated in FIG. 1. Thus, the second drum 206 is effectively a satellite of the first drum 106 with the peripheries thereof in relatively close proximity to each other. As described in more detail below with reference to FIG. 2, as a result of the arrangement with the axes of rotation R1 and R2 of the first drum 106 and the second drum 206 being substantially parallel in a vertical plane but simultaneously somewhat offset in the horizontal direction, a particularly space-saving arrangement is provided which also ensures a good transfer of the second components C2 of the absorbent core from the second air-laying means 200 onto the first components C1 in the first air-laying means 100.

As in the case of the first drum 106, the periphery of the second drum 206 comprises a plurality of forming cavities or moulds 208 which are optionally exchangeable. Inside the periphery of the second drum 206, there is a second means for generating an underpressure 210 such as a suction box which has a shape and dimensions adapted to the shape of the second drum and the outlet end of the second duct 204 to provide the optimal pressure difference and area for generating the second component of the absorbent core in the second cavities 208 during rotation of the second drum 206. Similarly as in the case of the first components. C1, the second components C2 are produced by blowing the mixture of fibrous material and discrete particles under pressure. by means of the second fan 202 through the second duct 204 onto the perforated base of the second cavities 208. The mixture collects there as a substantially uniform dispersion also under the influence of the underpressure generated by the second suction box 210. The second component C2 is formed on the perforated base of the second cavities 208 which, in the separate second air-laying means 200, can be entirely different, especially smaller in perforation size, than the perforated bases of the first cavities 108 in the first air-laying means 100 so as to hold back the relatively small discrete particles of the dispersed mixture and the fibrous material forming the second component C2. The air passes through the perforated second cavities 208 into second suction box 210.

A third underpressure source 212 such as a vacuum or suction box is arranged downstream of the second suction box 210 as seen in the direction of rotation A2 of the second drum 206. Further, as seen in this direction of rotation A2, the third suction box 212 is arranged beyond the peripheral area of the second drum 206 across which the outlet of the second duct 204 extends. This second section box 212 is provided to maintain the second components C2 in the second cavities 208 after their formation and before they are transferred onto a respective first component C1 in a first cavity 108 of the first air-laying means 100.

In the first air-laying means 100, a fourth underpressure source 112 in a form of a vacuum or suction box or the like is provided downstream of the first suction box 110 as seen in the direction of rotation A1 of the first drum 106. This fourth suction box 112 holds the first components in the first cavities 108 after they have been conveyed beyond the area between the first duct 104 and the first suction box 110 in which they were formed. Additionally, by being sufficiently extended in the direction of rotation A1 of the first drum 106, the fourth suction box 112 also acts to enhance the process of transfer of the second components C2 from the second cavities 208 of the second air-laying means 200 onto the respective first components C1 in the first cavities 108 of the first air-laying means 100, as described in more detail below.

The fourth suction box 112 of the first air-laying means also extends beyond the transfer zone in the direction of rotation A1 of the first drum 106 to hold the first and second components C1 and C2 in the first cavities 108. In accordance with the first preferred embodiment of the inventive apparatus as illustrated in FIGS. 1 and 2, a third fibrous component C3 of the absorbent core is then formed on top of the first and second components C1 and C2 (see FIG. 2). For this purpose, a third air fan 122 supplied with fibrous material or the like, possibly in a similar manner to that described above with reference to the first fan 102, and is connected to the outside periphery of the first drum 106 and the forming cavities 108 thereon by means of a third forming duct 124. The outlet end of the third forming duct 124 at the first drum 106 is appropriately shaped and dimensioned to be adapted to the shape of the first drum 106 and to provide a sufficient area for formation of the third components C3 in the first cavities 108 on the first and second components C1 and C2 already present therein Further, a fifth underpressure generating means 126 such as a vacuum or suction box or the like, is provided inside the periphery of the first drum 106 and the cavities 108 opposite and in substantial correspondence with the outlet end of the third duct 124 to create the required differential pressure for formation of the third components C3 of the absorbent core.

Figure 2:
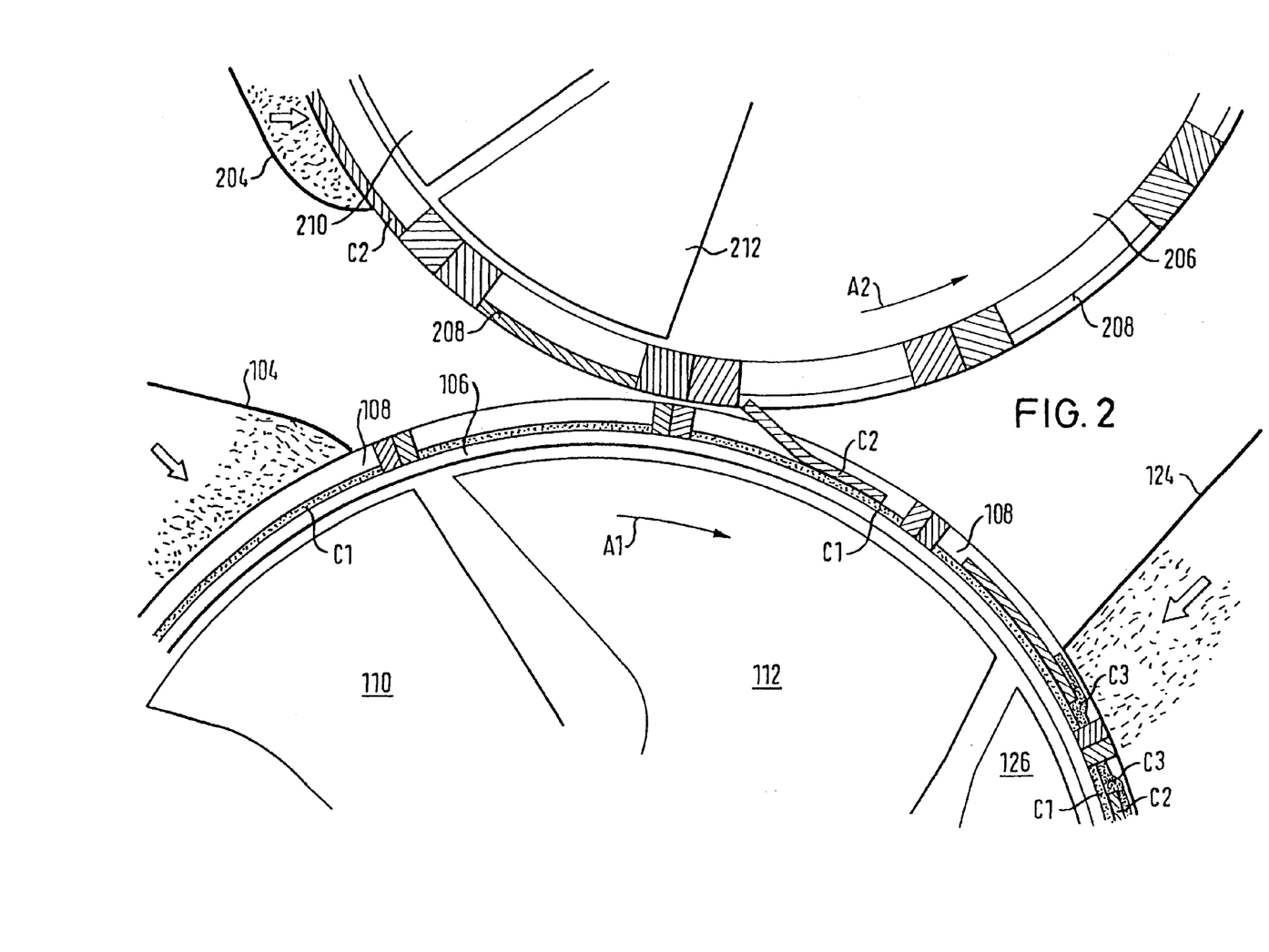
FIG. 2 shows a cross-sectional side view of a detail of the apparatus in FIG. 1.

With reference to FIGS. 1 and 2, the method of operating of the inventive apparatus according to the first preferred embodiment is described in the following.

Fibrous material, for example, fiberized pulp, is introduced into the first fan 102 of the first air-laying means 100 together with air and conveyed in the air-flow produced by the fan in the first forming duct 104 towards the first forming element or drum 106. The fibrous material is transported in this manner to the bottom of the perforated first cavities 108 on the periphery of the perforated first forming or drum element 106 as the first cavities 108 pass the outlet of the first duct 104 during rotation of the first drum 106. The forming cavities 108 have perforated bottoms formed, for example, of a mesh such as a wire mesh screen. With reference to FIG. 2, it will be noted that the first cavities 108 are relatively deep as seen in the radial direction of the first drum 106 so as to be able to each accommodate the first fibrous component C1, formed of fibers conveyed through the first duct 104, and the second component C2 and the third component C3 subsequently formed as described hereinafter.

The underpressure created in the first suction box 110 enhances the formation of the fibrous first components C1 in the cavities 108 when these are located beneath the first duct 104. Thus, the underpressure created in the first suction box 110 is lower than the pressure created by the fan 102 within the duct 104 so that the fibers are caused to gather on the perforated bottom of the first cavities 108, the fibrous material being held back by said perforated bottom while the air is sucked therethrough into the first suction box 110. The first cavities 108 with the first components C1 of the absorbent core formed therein then leave the area of influence of the first duct 104 and the first suction box 110 in the direction of rotation A1 of the first drum 106 and move into the area of influence of the fourth suction box 112 and the region of closest contact of the first cavities 108 with the second cavities 208 of the second air-laying means 200 in the transfer zone. Thus, during this phase of the production cycle, the first component C1 is maintained within the respective first cavity 108, firstly by the underpressure created in the first suction box 110 and subsequently by the underpressure created in the effectual area of the fourth suction box 112.

Meanwhile, in the second air-laying means 200, fibrous material such as fiberized pulp, and discrete particles such as a powder or granules of absorbent material, for example super-absorbent gelling material, are conveyed by the air flow produced by the second fan 202 through the second forming duct 204 towards the second forming element or drum 206 and the second forming cavities 208. In the preferred embodiment described herein with reference to FIGS. 1 and 2, the fibrous material and discrete particles are advantageously united before being supplied to the second fan 202 so that they are substantially uniformly mixed therein into a dispersion of fibrous material and discrete. particles before the fibrous material can form flocks. This mixture is then conveyed through the second duct 204 into the perforated second cavities 208 on the periphery of the rotating second drum 206 to form the second components C2 of the absorbent core. As shown in more detail in FIG. 2, the second cavities 208 have a depth as seen in the radial direction of the second drum 206 which is shallower than the depth of the first cavities 108 of the first air-laying means. This is because only a second component C2 is formed in the second air-laying means 200 in this embodiment of the inventive apparatus so that the depth of cavities 208 can substantially correspond to the final depth of the second component C2. This has the advantage of reducing the height through which each second component C2 must be transferred when it is placed on the first component C1 in the first air-laying means 100. This measure enhances the accuracy of placing or targeting the second component C2 onto a first component C1 in a first cavity 108.

The formation of the second components C2 with a substantially uniformed dispersion of fibrous material and discrete materials supplied through the second duct 204 onto the perforated bottom of the second cavities 208 is enhanced by the generation of an underpressure in the second suction box 210 arranged opposite the effectual area of the duct 204 on the inside of the perforated bottoms of the second cavities 208 with respect to the periphery of the second drum 206. The formed second components C2 then leave the area of influence of the second duct 204 and the second section box 210 in the direction of rotation A2 of the second drum 206 and pass into the effectual area of the third suction box 212 of the second air-laying means 200 and towards the region of transfer of the second components C2 onto the first components C1 in the first cavities 108. The third suction box 212 thus acts to hold the second components in the second cavities 208 against the influence of, for example, gravitational force and also prevents the undesirable loss of discrete particles. However, to further prevent the loss of discrete particles, it is possible to extend the downstream end of the second duct 204 in the direction of arrow A2 as compared to that illustrated in FIGS. 1 and 2 and closer to the second component transfer region. Alternatively, a plate can be provided covering the outside of the second cavities 208 and the formed second components C2 between the end of the second forming duct 204 and the area of transfer of the second components C2 onto the first components C1 to hold back the discrete particles and increase the effect of the underpressure on the second component.

As especially illustrated in FIG. 2, after a second cavity 208 with a second component C2 formed therein leaves the area of influence of the third suction box 212, the second component C2 is placed under the influence of the underpressure or suction of the fourth suction box 112 such that it is gradually drawn out of the second cavity 208, first by its leading end. As the rotation of the second drum 206 in the direction of arrow A2 and the rotation of the first drum 106 in the direction of arrow A1 continues, gradually the whole length of the second component C2 is drawn out of the second cavity 208 into the first cavity 201 such that it is placed or targeted under controlled conditions at the desired position on the first component C1 already formed within the first cavity 108. The underpressure in the fourth suction box 112 maintains the second component C2 on the first component C1 in the first cavity 108 and is preferably adjusted to have the effect of causing some of the fibers of the respective components to entangle with each other such as to increase the adhesion between the respective components. By appropriately adapting the respective speeds of the first and second drums 106 and 206, the transfer of each second component C2 onto the associated first component C1 within the respective first cavity 108 occurs at the desired precise location required for the final absorbent product. The emptied second cavities 208 of the second air-laying means 200 are then further rotated in the direction A2 until they again enter the area of influence of the second duct 204 and the second suction box 210 where a new second component C2 is formed.

As also shown in more detail in FIG. 2, after a second component C2 has been transferred onto a first component C1 in a first cavity 108, further rotation of the first drum 106 brings the superimposed first and second components C1 and C2 into the area of influence of the third forming duct 124 and the fifth suction box 126. As a result, fibrous material conveyed in the air stream created by the third fan 122 is blown along the third duct 124 into the first cavity 108 and a third fibrous component C3 of the absorbent core is formed on top of the first and second components C1 and C2 in a similar manner as the formation of the first component C1 by means of the first fan 102, the first duct 104 and the first suction box 110. On account of the underpressure or depression created therein, the fifth suction box 126, which takes effect in substantially the same area as the third duct 124 but on the opposite side of the first cavities 108 to said third duct, enhances the formation of the third component C3 under a differential pressure between it and the third duct 124 and, by appropriate adjustment, the differential pressure can be used to entangle fibers of the first, second and third components C1 to C3 and improve the adhesion therebetween.

Finally, upon further rotation of the first drum 106 in the direction of arrow A1, the completed absorbent core comprising the first, second and third components C1, C2 and C3, respectively, leaves the area of influence of the third duct 124 and the fifth suction box 126 and is transferred out of the first cavity 108 onto the conveying means 300. If required, a sixth suction box (not shown) with a low underpressure can be provided downstream of the fifth suction box 126 as seen in the direction of rotation A1 of the first drum 106 to hold the absorbent core within the first cavity 108 until it is removed therefrom, for example, under the influence of gravitational force and, additionally, a possible further underpressure created beneath the conveying means 300. The emptied first cavity 108 then continues in the direction of rotation A1 of the first drum 106 to return into the area of influence of the first duct 104 and the first suction box 110 where the above-described cycle for producing triple-layered absorbent cores newly begins and a first component C1 of the absorbent core is formed therein. With reference to the detailed illustration in FIG. 2, it is also to be noted that the first cavity depth in the radial direction of the first drum 106 is chosen such as to accommodate all three components of the absorbent core C1, C2 and C3.

Figure 3:
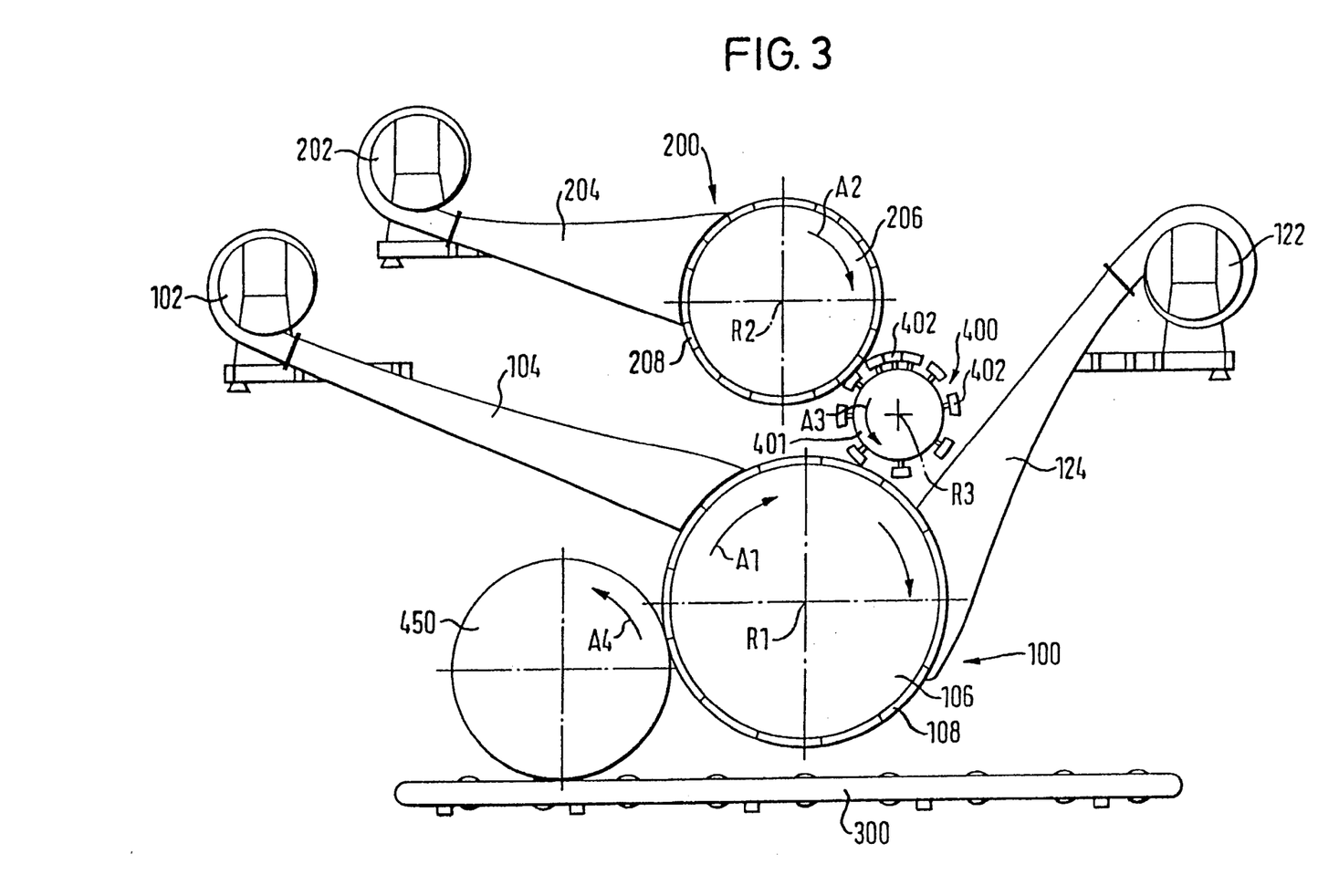
FIG. 3 shows a partially cut-away side view of a second preferred embodiment of an apparatus according to the present invention similar to the apparatus of FIG. 1 but with a transfer means.

FIG. 3 shows an alternative preferred embodiment of the inventive apparatus. Like parts to the preferred embodiments described above with reference to FIGS. 1 and 2 are designated with the same reference numerals. The alternative embodiment shown in FIG. 3 differs from that shown in FIGS. 1 and 2 essentially in two aspects. Firstly, as an alternative to the direct transfer of the second component C2 from the second air-laying means 200 onto a first component C1 already formed in a first cavity 108 of the first air-laying means 100, a transfer means 400 as shown in FIG. 3 can be provided. The transfer means 400 preferably comprises a cylindrical drum 401 rotated about an axis R3 in the direction of arrow A3 shown in FIG. 3. As seen in the drawing plane of cross section of FIG. 3, the axis of rotation R3 of the transfer means 400 is substantially parallel to the axis of rotation R1 of the first drum 106 and the axis of rotation R2 of the second drum 206. Provided on the periphery of the cylindrical drum 401 is a plurality of pick-up means 402, which may comprise suction shoes or the like. The transfer means 400 acts in the manner of an accelerator with respect to the pick-up means or suction shoes 402 such that these are rotatable around the periphery of the transfer means 400 at a variable orbital distance from the axis of rotation R3 of the pick-up means 402 and the transfer means 400 and with an increased or decreased rotational speed during their orbiting around the periphery of the cylindrical drum 401. The variation in speed and the variable orbital distance of the pick-up means is effected so as to be able to compensate any variation in the distance of the pick-up means from the second cavities 208 and the first cavities 108 depending on the diameters of the two drums, the size and/or number of cavities etc.

Firstly, in operation, the respective pick-up means 402 is rotated at a certain radial distance from the axis of rotation P3 thereof into contact with a second component C2 which has already been formed in a second cavity 208 of the second air-laying means 200. After picking up the second component C2, for example by way of a suction action if the pick-up means 402 are provided as suction shoes, the respective pick-up means is accelerated in the direction of rotation of arrow A3 together with the second component C2 towards a first cavity 108 of the first air-laying means 100 while its orbital distance from the axis of rotation R3 of the transfer means 400 is increased. At the maximum orbital distance, the pick-up means 402 and the second component C2 thereon reaches the periphery of the first drum 106 and the transfer of the second component C2 onto the first component C1 in the first cavity 108 is effected. The respective pick-up means 402 is then decelerated in the direction of rotation of arrow A3 and its orbital distance from the axis of rotation R3 of the transfer means 400 is decreased until it returns to the location where it again picks up a new second component C2 to repeat the cycle.

This particular transfer arrangement provides various advantages. In one embodiment, if the speeds and diameters of the first drum 106 and the second drum 206 are the same when, for example, the length of the first component C1 formed in the first air-laying means 100 and the length of the second component C2 formed in the second air-laying means 200 are the same, the number of the first cavities 108 on the first drum 106 and the number of second cavities 208 on the second drum 206 are the same. Alternatively, if the length of the first cavities 108 and the first components C1 formed therein is greater than the length of the second cavities 208 and the. second components C2 formed therein, for the same rotational speed of the two drums, the diameter of the first drum 106 must be greater than that of the second drum 206. Therefore, it is possible that different first and second drum diameters must be provided depending on the required length of the respective components of the absorbent core and the number of the respective cavities. However, with a transfer means 400 as described above, there is no requirement for such measures because the transfer means can compensate for any desirable number of first cavities 108 or second cavities 208 provided on the respective first and second drums 106 and 108 since the acceleration and deceleration of the pickup means 402 of the transfer means 400 compensates for the different number of cavities in the first and second drums that pass a reference point in any given time period. Further, the transfer means can compensate for different distances if a change in drum diameters is required.

A further advantage of the transfer means 400 as described above is the improvement in transfer or delivery of the second component C2 onto the first component C1 in the first cavity 108 of the first air-laying means. In the preferred embodiments described with reference to FIGS. 1 and 2, the smallest distance between the first and second cavities 108 and 208 of the first and second air-laying means 100 and 200 in the transfer zones is minimised so that the transfer distance of the second component C2 onto the first component C1 is as small as possible to ensure a good transfer. However, even in the case of a close arrangement of the first and second drums 106 and 206, on account of the first cavity being large enough not to be filled when only the first component C1 is formed therein so as to provide sufficient space for the second (and possibly third) components to be subsequently accomodated, there is still a relatively large distance through which the second component C2 must be transferred. However, the variable orbital distance of rotation of the pick-up means 402 in the transfer means 400 removes such a transfer gap within which the second component C2 is not guided in a positively controlled manner since it is held by the pick-up means 402 from the time of its removal from the second cavity 208 until its placement on the first component C1 in the first cavity 108. Therefore, the transfer means 400 provides an improved positive transfer or targeting of the second component C2 onto the first component C1.

FIG. 3 also shows a further alternative embodiment to the arrangement described above with reference to FIGS. 1 and 2. Instead of directly transferring the final absorbent core out of the first cavities 108 on the periphery of the first drum 106 onto the conveying means 300, a cylindrical transfer drum 450 or the like arranged between the first drum 106 and the conveying means 300 and rotated in the direction of arrow A4 as shown in FIG. 3 can be provided to pick up each final absorbent core out of the first cavities 108 of the first air-laying means 100 and transfer this onto the conveying means 300. The speed of rotation or the diameter of the transfer drum 450 can be varied as desired to increase or decrease the speed of transfer of the final absorbent core onto the conveying means 300.

The present invention is not limited to the embodiments described above with reference to FIGS. 1 to 3. Rather, it is defined by the scope of the claims attached hereto. For example, the rotatable first and second drums can be replaced by perforated belts or the like having forming cavities formed therealong for the respective absorbent core components. The belts can converge on each other and deliver one component onto a component on another belt in a similar manner to the embodiments described above with reference to the Figures. Further, the pressure in the fans and underpressure generating means such as the suction boxes of the first and second air-laying means and, if applicable, the conveying means can be altered as desired to create the optimum conditions for air-laying or transferring the various components to form the final absorbent core. Thus, the higher pressure of the blowing air fans to convey the fibrous material, possibly together with discrete particles, and the suction or underpressure to draw these into the respective forming cavities can be selected individually and adapted to each other to produce the optimal air-laying results. It is also evident that it is simple to produce a dual-layer absorbent core as opposed to a triple-layer absorbent core described above with reference to FIGS. 1 to 3 by simply placing the third air fan 124 out of operation.

As already explained, since the first and second air-laying means are separated from each other, this provides the particular advantage of being able to independently select and adjust different forming conditions for the respective components of the final absorbent core, including different pressures, cavity shapes, dimensions and perforation sizes, the use of different materials or material mixtures etc. Additionally, depending on the diameters of the first and second drums 106 and 206 described with reference to FIGS. 1 to 3 and, if applicable, of the transfer means 400, their rotary speeds can be adapted to each other such that a second component C2 is always supplied in a precise position on each of the first components C1. Naturally, however, also the number and lengths of the respective cavities and, if applicable, the number of pick-up means in the transfer means must be taken into account in selecting the rotary speeds so as to achieve the optimal results both in terms of the speed of the process and the quality of the final product.

It should also be noted that the shapes of any of the forming ducts and the housings of the underpressure generating means such as the suction boxes can be chosen such that the effective pressure of the air flows produced along the peripheries of the respective forming elements upon which they act, varies as desired in the direction of movement of the associated forming elements or drums and the cavities thereon to increase or decrease the effective force of the air flow on the components of the absorbent cores formed or being formed in the cavities. This further improves the ability to safely and effectively form, hold or remove them in the cavities depending on their location within the production process. Examples of various shapes of the ducts and underpressure generating means are illustratively indicated by the different cross-sectional shapes of the ducts as shown in the Figures,. However, the present invention is not limited to these shapes and any appropriate shape to achieve the desired effect will be readily determinable by the skilled person.

What is claimed is:

1. An apparatus for forming air-laid fibrous absorbent cores, comprising:
    a first supply of air-entrained fibrous material;
    a first air-laying means connected with the first supply of air-entrained fibrous material and having a movable first perforated forming element for forming a first air-laid component of an absorbent core;
    a supply of air-entrained fibrous material and discrete particles of absorbent material;
    a second air-laying means connected with the supply of air-entrained fibrous material and discrete particles, the second air-laying means having a movable second perforated forming element for forming a second air-laid component of the absorbent core;
    the second air-laid component comprising a mixture of dispersed fibrous material and discrete particles;
    the second air-laying means being positioned with respect to the first air-laying means so as to transfer a formed second component from the second forming element directly onto a formed first component on the first forming element of the first air-laying means.

2. The apparatus according to claim 1, further comprising a second supply of air-entrained fibrous material separate from the first supply and also connected to the first forming element of the first air-laying means at a position downstream of the first supply and the location of transfer of the second component onto the first component so as to form a third air-laid component of the absorbent core on the first and second components while these are still on the first forming element.

3. The apparatus according to claim 2, wherein the first supply of air-entrained fibrous material comprises a source of fibrous material connected to a first air fan, and the second supply of air-entrained fibrous material comprises a source of fibrous material connected to a second air fan, and each air fan is connected to the first forming element.

4. The apparatus according to claim 3, wherein the supply of air-entrained fibrous material and discrete particles comprises a source of fibrous material and a source of discrete particles, each source being connected to a third air fan for mixing the fibrous material and the discrete particles and the third air fan being connected to the second forming element.

5. The apparatus according to claim 1, wherein the first and second forming element comprise at least one forming cavity having a perforated base.

6. The apparatus according to claim 5, wherein the forming cavity of the first forming element is larger than the forming cavity of the second forming element.

7. The apparatus according to claim 5, wherein each cavity in the forming element has a length defined in the direction of movement of the forming element and a width measured transversely to the direction of movement.

8. The apparatus according to claim 7, wherein the cavity in the first forming element has a length greater than that of the cavity in the second forming element.

9. The apparatus according to claim 7, wherein the cavity in the first forming element has a width greater than that of the cavity in the second forming element.

10. The apparatus according to claim 4, wherein a respective forming duct for the first and for the second supply of air-entrained fibrous material is connected between the respective air fan and the first forming element, and each forming duct has a width substantially corresponding to the width of the cavity in the first forming element.

11. The apparatus according to claim 10, wherein a forming duct for the supply of fibrous material and discrete particles is connected between the third air fan and has a width substantially corresponding to the width of an at least one forming cavity in the second forming element.

12. The apparatus according to claim 1, wherein the perforations in the first forming element have a largest dimension of approximately 1 mm.

13. The apparatus according to claim 1, wherein the perforations in the second forming element have a largest dimension of approximately 0.5 mm.

14. The apparatus according to claim 1, wherein the perforations in the first and second forming elements are formed by a screen.

15. The apparatus according to claim 1, wherein the first air-laying means comprises a first rotatable forming drum, and the second air-laying means comprises a second rotatable forming drum.

16. The apparatus according to claim 15, wherein the first and second forming elements are arranged on the periphery of the first and second forming drums, respectively.

17. The apparatus according to claim 15, wherein the second forming drum is arranged above the first forming drum.

18. The apparatus according to claim 1, wherein the first air-laying means comprises a transfer vacuum means for transferring the second component from the second air-laying means onto a formed first component on the first air-laying means.

19. The apparatus according to claim 1, wherein the first and second air-laying means comprise component vacuum means for forming a component on the respective forming element, and temporarily maintaining the formed component in position along the path of movement of the forming element.

20. The apparatus according to claim 1, further comprising transfer means positioned between the first and second air-laying means, and having at least one pick-up member for transferring a formed second component from the second air-laying means onto a formed first component on the first air-laying means.

21. The apparatus according to claim 20, wherein the at least one pick-up member is rotatable around the periphery of the transfer means at a variable orbital distance from the axis of rotation of the pick-up member.

22. The apparatus according to claim 1, further comprising a conveying means positioned adjacent the first air-laying means to receive an absorbent core from and to convey the absorbent core away from the first air-laying means.

23. The apparatus according to claim 1, wherein the perforations in the first forming element have a largest dimension of approximately 0.2 mm, and the perforations in the second forming element have a largest dimension of approximately 0.05 mm.

24. A method of forming air-laid fibrous absorbent cores, the method comprising the steps of:

a) providing a first stream of air-entrained fibrous material;

b) forming from the first stream a first component on an absorbent core comprising air-laid fibrous material on a moving first perforated forming element;

c) providing a stream of mixed air-entrained fibrous material and discrete particles of absorbent material;

d) forming from the stream of air-entrained fibrous material and discrete particles a second component of the absorbent core comprising a mixture of dispersed fibrous material and discrete particles on a moving second perforated forming element;

e) directly transferring a formed second component from the second forming element onto a formed first component on the first forming element; and f) removing an absorbent core comprising the first and second components from the first forming element.

25. The method according to claim 24, wherein step f) alternatively comprises:

g) providing a second stream of air-entrained fibrous material; and h) forming from the second stream a third component of the absorbent core comprising air-laid fibrous material on the formed first and second components on the first forming element to form the absorbent core, and then removing the absorbent core comprising the first, second and third components from the first forming element.

26. The method according to claim 24, wherein the second component is formed so as to be smaller than the first component.

27. The method according to claim 24, wherein the second component is formed with a length measured in the moving direction of the second forming element which is shorter than the length of a formed first component measured in the moving direction of the first forming element.

28. The method according to claim 24, wherein the second component is formed with a width measured transversely to the moving direction of the second forming element which is narrower than the width of a formed first component measured transversely to the moving direction of the first forming element.

29. The method according to claim 24, wherein the stream of air-entrained fibrous material and discrete particles is mixed in an air fan before being formed on the second forming element.

30. The method according to claim 24, wherein the first and second perforated elements rotate during formation of the first and second components.

31. The method according to claim 24, further comprising the steps of creating an underpressure at the first and second forming elements to form the first and second components thereon, and to temporarily maintain the formed components in position along the direction of movement of the forming elements.

32. The method according to claim 24, wherein step e) is performed by providing a transfer means with at least one pick-up member between the first and second forming elements, and transferring the formed second component with the pick-up member from the second forming element onto a formed first component on the first forming element.

33. The method according to claim 32, further comprising the step of transferring the formed second component by rotating the at least one pick-up member around the periphery of the transfer means at a variable orbital distance from the axis of rotation of the pick-up member.

34. The method according to claim 24, wherein perforations of the first forming element have a largest dimension of approximately 1 mm.

35. The method according to claim 24, wherein perforations of the second forming element have a largest dimension of approximately 0.5 mm.

36. The method according to claim 24, wherein perforations of the first forming element have a largest dimension of approximately 0.2 mm, and perforations of the second forming element have a largest dimension of approximately 0.05 mm.

37. The method according to claim 24, wherein the second component is formed under a differential pressure across the second forming element of approximately 30,000 Pa.

* * * * *